(12) United States Patent
Güimil et al.

(10) Patent No.: US 7,355,036 B2
(45) Date of Patent: Apr. 8, 2008

(54) TWO-STAGE PROTECTIVE GROUPS FOR THE SYNTHESIS OF BIOPOLYMERS

(75) Inventors: Ramon Güimil, Heidelberg (DE); Matthias Scheffler, Hirschberg/Leutershausen (DE); Peer F. Stähler, Mannheim (DE); Barbro Beijer, Nussloch (DE)

(73) Assignee: Febit AG, Mannheim (DE)

( * ) Notice: Subject to any disclaimer, the term of this patent is extended or adjusted under 35 U.S.C. 154(b) by 469 days.

(21) Appl. No.: 10/482,744

(22) PCT Filed: Jul. 3, 2002

(86) PCT No.: PCT/EP02/07389

§ 371 (c)(1),
(2), (4) Date: Jan. 5, 2004

(87) PCT Pub. No.: WO03/004510

PCT Pub. Date: Jan. 16, 2003

(65) Prior Publication Data

US 2004/0197851 A1    Oct. 7, 2004

Related U.S. Application Data

(60) Provisional application No. 60/314,306, filed on Aug. 24, 2001.

(30) Foreign Application Priority Data

Jul. 3, 2001   (DE) ................................ 101 32 025

(51) Int. Cl.
*C07H 21/04* (2006.01)
(52) U.S. Cl. .................................... 536/25.3
(58) Field of Classification Search ............... 435/68.1, 435/91.2; 536/25.3
See application file for complete search history.

(56) References Cited

U.S. PATENT DOCUMENTS 5,763,599 A    6/1998 Pfleiderer et al.

FOREIGN PATENT DOCUMENTS

WO    WO 01/08677 A1    2/2001

OTHER PUBLICATIONS

Sekine et al The Chemical Society of Japan, 1985, 58, 336-33.*
Happ et al Nucleosides and Nucleotides, 1988, 7, 813-816.*
March, Advanced Organic Chemistry, 4th edition, 1992, 242-246.*
Erwin Happ, et al., "New Trityl-Based Protecting Groups with a Mild Two-Step Removal", Nucleosides & Nucleotides, vol. 7, Nos. 5&6, (1988), pp. 813-816.
Mitsuo Sekine, et al., "4,4',4"-Tris(levulinoyloxy)trityl as a New Type of Primary Hydroxyl Protecting Group", Bull. Chem. Soc. Jpn., vol. 58, No. 1, (1985), pp. 336-339.
Mitsuo Sekine, et al., "4,4',4"- Tris(benzoyloxy)trityl) as a New Type of Base-Labile Group for Protection of Primary Hydroxyl Groups", J. Org. Chem., vol. 48, (1983), pp. 3011-3014.
E. Happ, C. Scalfi Happ: "New trityl-based protecting groups with a mild two-step removal", Nucleosides & Nucleotides, vol. 7, 1988, pp. 813-816.

* cited by examiner (Continued)

*Primary Examiner*—Shaojia Anna Jiang
*Assistant Examiner*—Ganapathy Krishnan
(74) *Attorney, Agent, or Firm*—Rothwell, Figg, Ernst & Manbeck p.c.

(57) ABSTRACT

The invention relates to a method for the synthesis of a nucleic acid by gradual breakdown from protected synthesis building blocks carrying two-stage protective groups. The two-stage protective groups are split by means of a first exposure step and a subsequent chemical treatment step 22 Claims, 8 Drawing Sheets

A

B

TWO-STAGE PROTECTIVE GROUPS FOR THE SYNTHESIS OF BIOPOLYMERS

CROSS REFERENCE TO RELATED APPLICATION

This application is a 35 USC § 371 National Phase Entry Application from PCT/EP02/07389, filed Jul. 3, 2002, and designating the U.S., which claims priority of 60/314,306 filed Aug. 24, 2001.

The present invention relates to a process for the synthesis of biopolymers by stepwise assembly from protected synthetic building blocks which carry two-stage protective groups. The two-stage protective groups are activated by a first illumination step and eliminated by a subsequent chemical treatment step.

The technology of light-controlled synthesis of biopolymers using photolabile protective groups opens up the possibility of producing biochips in situ by synthesis from monomeric and oligomeric building blocks. Biochips have gained a very considerable importance for research and diagnosis since they permit rapid and highly parallel processing of complex biological problems. However, chips of the highest quality are required for this, so that there is a great interest in novel and more efficient synthetic methods.

Photolabile nucleoside derivatives are used in the light-controlled synthesis of nucleic acid chips. In this connection, the assembly of the chain of nucleic acid fragments normally takes place using phosphoramidite synthons. The building blocks each carry a temporary photoprotective group which can be removed by incident light. The principle of the synthesis provides for a cyclic sequence of condensation and deprotection steps (by light). The efficiency with which such a light-controlled synthesis can take place is determined essentially by the photolabile protective groups used, in particular by the efficiency with which they can be removed in the irradiation step. The photoprotective groups used to date for light-controlled synthesis are normally the protective groups NVOC (S. P. A. Fodor et al., Science 251 (1991), 767 ff.), MeNPOC (A. C. Pease et al., Proc. Natl. Acad. Sci. 91 (1994), 5022 ff.), DMBOC (M. C. Pirrung, J. Chem. 60 (1995), 1116 ff.) and NPPOC (A. Hassan et al., Tetrahedron 53 (1997), 4247 ff.). Further known photolabile protective groups in nucleoside and nucleotide chemistry are o-nitrobenzyl groups and their derivatives (cf., for example, Pillai, Org. Photochem. 9 (1987), 225; Walker et al., J. Am. Chem. Soc. 110 (1988), 7170). A further photolabile protective group which has been proposed is the 2-(o-nitrophenyl)ethyl group (Pfleiderer et al., in: "Biophosphates and their Analogues—Synthesis, Structure, Metabolism and Activity", ELSEVIER Science Publishers B. V. Amsterdam (1987), 133 ff.) and derivatives thereof (WO 97/44345 and WO 96/18634).

The photolabile protective groups currently used for light-controlled synthesis of nucleic acids (e.g. NVOC, MeNPOC, NPPOC) are generally distinguished by a comparatively low absorption coefficient at the wavelength of the incident light. Irradiation of photolabile nucleoside derivatives normally takes place with high pressure Hg lamps at a wavelength of 365 nm. The result of the low absorption coefficient of the photolabile protective group used at this wavelength is that only a very small proportion of the incident light can be utilized for excitation of the molecules. In addition, the photolabile protective groups used are mostly colorless derivatives. The result of this in turn is that it is not possible during the synthesis to detect by simple spectroscopic methods whether the photolabile protective group is still present on the nucleoside derivative or has already been partly or completely abstracted by the input of light. The abstraction process can thus be followed only with difficulty or not at all.

Muller et al. (Helvetica Chim. Acta 84 (2001), 3735-3741) describe a photolabile protective group consisting of an MeNPOC group to which a fluorescent coumarin derivative is coupled via an amino linker. This photolabile protective group is employed for synthesizing oligonucleotides on DNA microarrays. Elimination of the photolabile protective group takes place in a single step by irradiation.

The present invention provides a novel protective group with which the activation step is induced by light and the actual deprotection step at the reaction site takes place by chemical means, e.g. acid catalysis (FIG. 1). This novel protective group, and molecules carrying this protective group, can be employed for the synthesis of biopolymers.

One aspect of the invention is thus a process for the synthesis of biopolymers by stepwise assembly from synthesis building blocks which carry protective groups, with use of at least one synthesis building block which carries a two-stage protective group which is activated by an illumination step and is eliminated by a subsequent chemical treatment step. The chemical treatment step preferably comprises a treatment with base, a treatment with acid, an oxidation, a reduction or/and an enzymatic reaction. The chemical treatment step particularly preferably comprises an acid treatment.

In a particularly preferred embodiment of the invention, a derivatized trityl group is used as two-stage protective group. Trityl groups are notable for their excellent ease of elimination, in particular by treatment with acid. The two-stage trityl protective groups of the invention are, by contrast, not acid-labile but are converted into an acid-labile form only after activation and elimination of one or more photolabile components. Particular preference is therefore given to the use of a synthesis building block which has a two-stage protective group and has the general formula I:

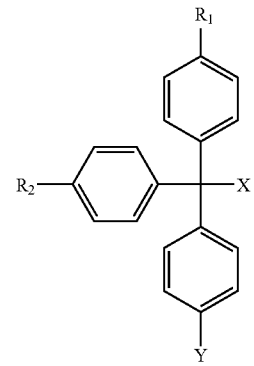

where $R_1$ and $R_2$ are each independently selected from hydrogen, $OR_3$, $O(CH_2)_n COOR_3$ and NHZ, $R_3$ comprises a $C_1$-$C_8$alkyl group, a $C_2$-$C_8$alkenyl group, a $C_2$-$C_8$alkynyl group or/and a $C_6$-$C_{20}$aryl group which may optionally have one or more substituents, X is the synthesis building block, Y is in each case independently a photoactivatable protective group, Z is an amino-protective group, n is an integer from 0 to 4, and where $R_1$ or/and $R_2$ may optionally be replaced by Y.

The alkyl, alkenyl and alkynyl groups may be linear or cyclic, straight-chain or branched. Preferred meanings of $R_1$ and $R_2$ are hydrogen, O-methyl, OCOO-methyl or a protected amino group, e.g. an amino group which has been converted into an amide function with a suitable carboxylic acid.

The invention also encompasses compounds which carry a plurality of photoactivatable protective groups, in particular compounds of the formula I in which at least one of $R_1$ or $R_2$ is replaced by a photoactivatable protective group Y.

It is possible by varying the radicals $R_1$ and $R_2$ and substituting one or both radicals by photoactivatable protective groups to adapt the lability to acid to the desired requirements.

The invention also encompasses compounds which carry one or more fluorescent groups, e.g. compounds in which Y is a fluorescent photoprotective group or/and $R_3$ and Z are fluorescent groups (R. Ramage, F. O. Wahl, Tetrahedron Lett., 34 (1993), 7133) or molecules in which the fluorescence has been introduced by substitution on the trityl framework (J. L. Fourrey et al., Tetrahedron Lett., 28 (1987), 5157).

These fluorescent groups can be employed for the quality control of biochips as long as the excitation and emission wavelengths do not interfere with the light-induced activation. This can take place for example in biochip supports as disclosed in WO 00/13018.

The photoactivatable group Y of the two-stage protective group may in principle be selected from any known photoprotective groups such as, for example, nitroveratryloxycarbonyl (NVOC), α-methyl-6-nitropiperonyloxycarbonyl (MeNPOC), 3,5-dimethoxybenzoincarbonate (DMBOC), 2-(o-nitrophenyl)propyloxycarbonyl (NPPOC), o-nitrobenzyl and derivatives thereof, 2-(o-nitrophenyl)ethyl and derivatives thereof.

If a plurality of photoactivatable groups Y are present, they may be identical or different.

The photoactivatable component Y of the two-stage protective group can be eliminated by an illumination step. Elimination of the group Y increases the lability of the remaining protective group, so that it can be eliminated by a subsequent chemical treatment step, while a two-stage protective group which still contains the photoactivatable component Y is substantially resistant to elimination under such conditions.

The process of the invention is employed for the synthesis of biopolymers, with the biopolymer to be synthesized being assembled stepwise from a plurality of synthesis building blocks. The process is particularly preferably employed for the synthesis of nucleic acids, e.g. DNA or RNA. However, it should be noted that the process is also suitable for the synthesis of other biopolymers such as, for example, peptides, peptide-nucleic acids (PNAS) or saccharides. The synthesis building block may be a monomeric building block, e.g. a nucleoside derivative, or else an oligomeric building block, e.g. a dimer or trimer, i.e. for example a di- or trinucleoside derivative. The synthesis building block is particularly preferably a phosphoramidite building block. It is, however, also possible to use other nucleotide synthesis building blocks, e.g. phosphate or phosphonate building blocks. A further possibility is also to employ linker or spacer building blocks, e.g. as phosphoramidites, as synthesis building blocks. Particularly preferred linkers or spacers as carriers of two-stage protective groups are described in DE 100 41 539.3.

The synthesis building blocks of the invention carrying a two-stage protective group generally have more strongly lipophilic properties than the synthesis building blocks used to date in the prior art. The solubility of the synthesis building blocks, especially of the phosphoramidite synthons, in organic solvents is increased through this lipophilicity. The more homogeneous reaction management made possible thereby leads to a higher coupling efficiency compared with the pure photolabile phosphoramidite synthons. Elimination of the colored trityl cation of the photoprotective groups of the invention, which has a considerably higher absorption coefficient than the elimination products of other photodeprotection processes, also opens up the possibility of direct online process monitoring. This leads to an improvement in the quality control of biochips.

The trityl group of the photoprotective groups of the invention additionally makes selective functionalization of the 5'-hydroxy function possible. This leads to an enormous reduction in costs, because separation of the 3'-5' isomers is dispensed with.

Particular preference is therefore given according to the present invention to phosphoramidite building blocks which carry the two-stage protective group on the 5'-O atom of the sugar, in particular of the ribose or of the deoxyribose.

The synthesis of the biopolymers can be carried out in a conventional way, for example on a solid phase. It is particularly preferred for a plurality of biopolymers carrying a different sequence of synthesis building blocks to be generated in situ in the form of an array on a single support.

Yet a further aspect of the invention are compounds of the general formula I

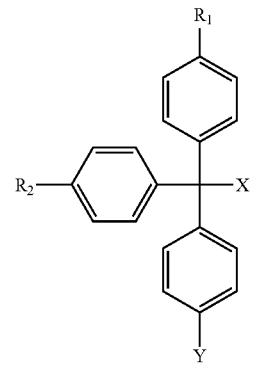

where $R_1$ and $R_2$ are each independently selected from hydrogen, $OR_3$, $O(CH_2)_n COOR_3$ and NHZ, $R_3$ contains a $C_1$-$C_8$ alkyl group or/and a $C_6$-$C_{20}$ aryl group which may optionally have substituents, X is a synthesis building block for the synthesis of biopolymers or a leaving group, Y is in each case independently a photoactivatable protective group, Z is an amino-protective group, n is an integer from 0 to 4, and where $R_1$ or/and $R_2$ may optionally be replaced by Y.

Substituents of alkyl, alkenyl, alkynyl and aryl groups are preferably selected from halogens, e.g. F, Cl, Br or I, OH, SH, —O—, —S—, —S(O)—, —S(O)$_2$—, NO$_2$, CN and NHZ, where Z is an amino-protective group. The substituents may be present one or more times on the relevant radical. Aryl groups may also comprise ring systems with heteroatoms such as, for example, O, N or/and S. Alkyl, alkenyl and alkynyl groups may be present in straight-chain, branched-chain or cyclic form and optionally be substituted by a $C_6$-$C_{20}$ aryl group, where the aryl group in turn may contain substituents as indicated above. Substituents of aryl groups are selected for example from —OH, halogen, —$C_1$-$C_4$-alkyl, —O—$C_1$-$C_4$-alkyl, where the alkyl groups may be substituted as indicated above.

If X is a leaving group, it is a group which can be eliminated when the compound (I) reacts with another compound. X is preferably a leaving group which can be eliminated by reaction with a nucleophile, where appropriate in the presence of an auxiliary base such as pyridine. Preferred examples of X are: Cl, Br, I, tosylate, mesylate, trifluorosulfonate etc.

Diagrammatic representation of the protective group concept of the invention is shown in FIG. 1. The synthesis building block (A) carries a two-stage protective group (B-C). In a first illumination step, the photolabile portion (B) of the protective group is eliminated. A second chemical treatment step, e.g. by addition of acid, eliminates the chemically labile component (C) of the protective group, so that the synthesis building block (A) is present in active form.

FIG. 2 shows an exemplary substance from a preferred class of two-stage protective groups of the invention. It is based on the acid-labile trityl group but contains in the p position of one phenyl radical a photolabile component (in this case the NPPOC group) which reduces or completely blocks the acid-sensitivity of the trityl group. Illumination and elimination of the photolabile component converts the protective group into an acid-labile form, and it can subsequently be eliminated in the presence of acid to release the unprotected synthesis building block.

Figure 1:
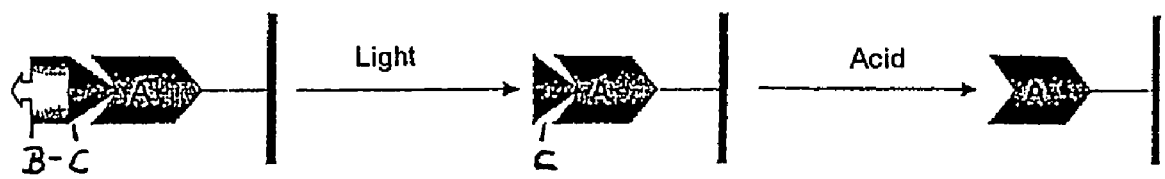
Figure 2:
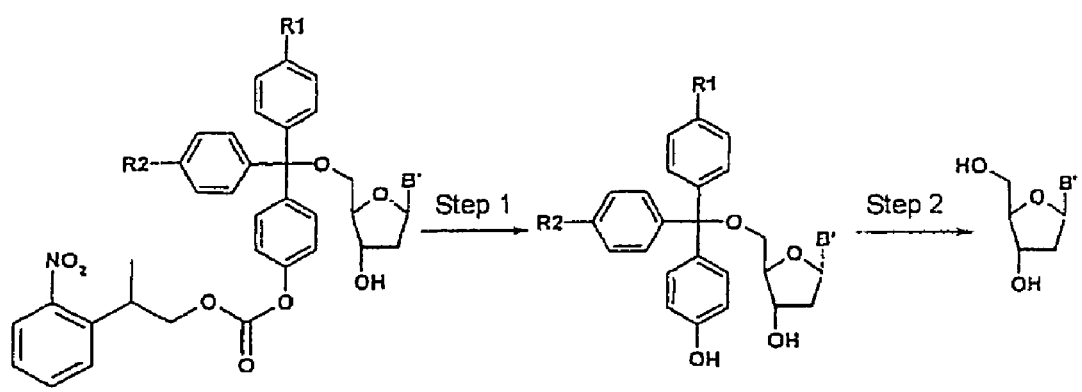
Figure 3:
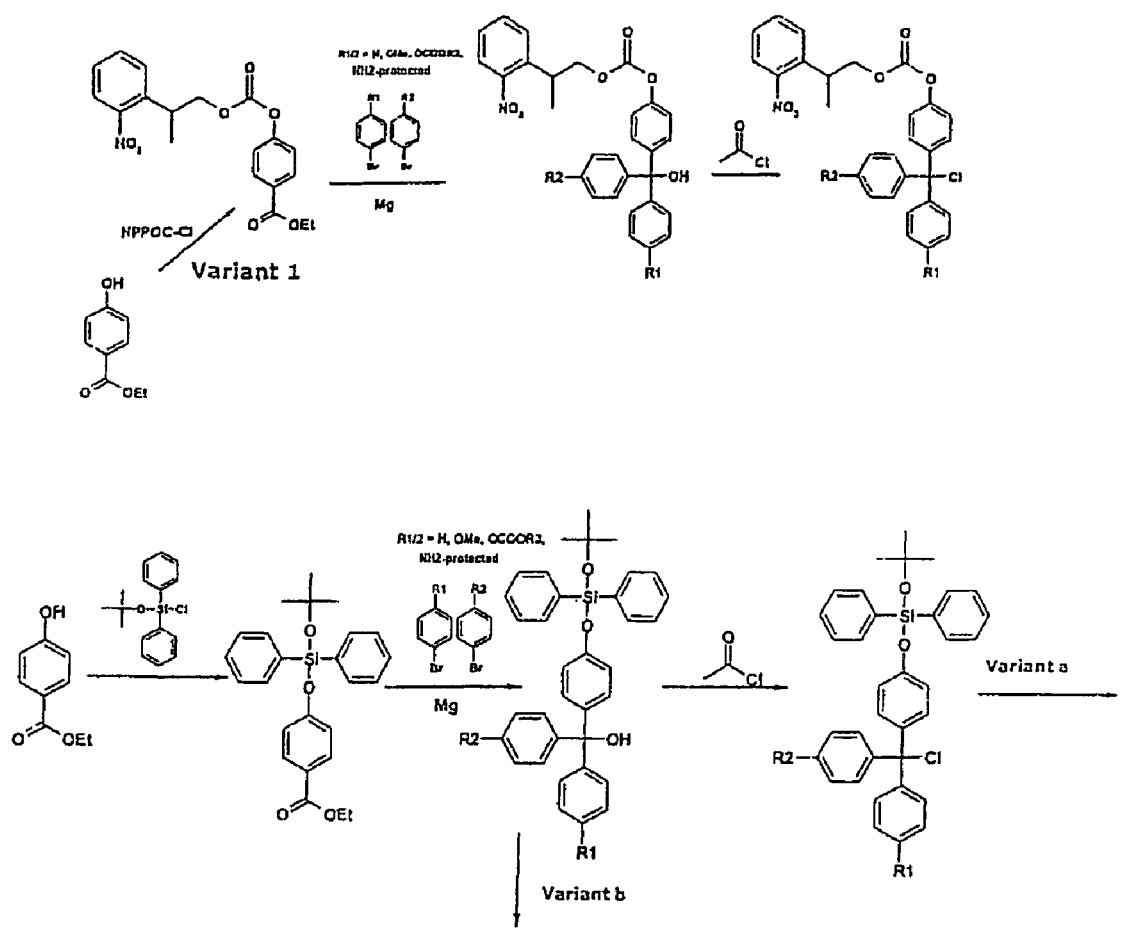
FIG. 3 shows two variants for the synthesis of a two-stage protective group of the invention.
Figure 4:
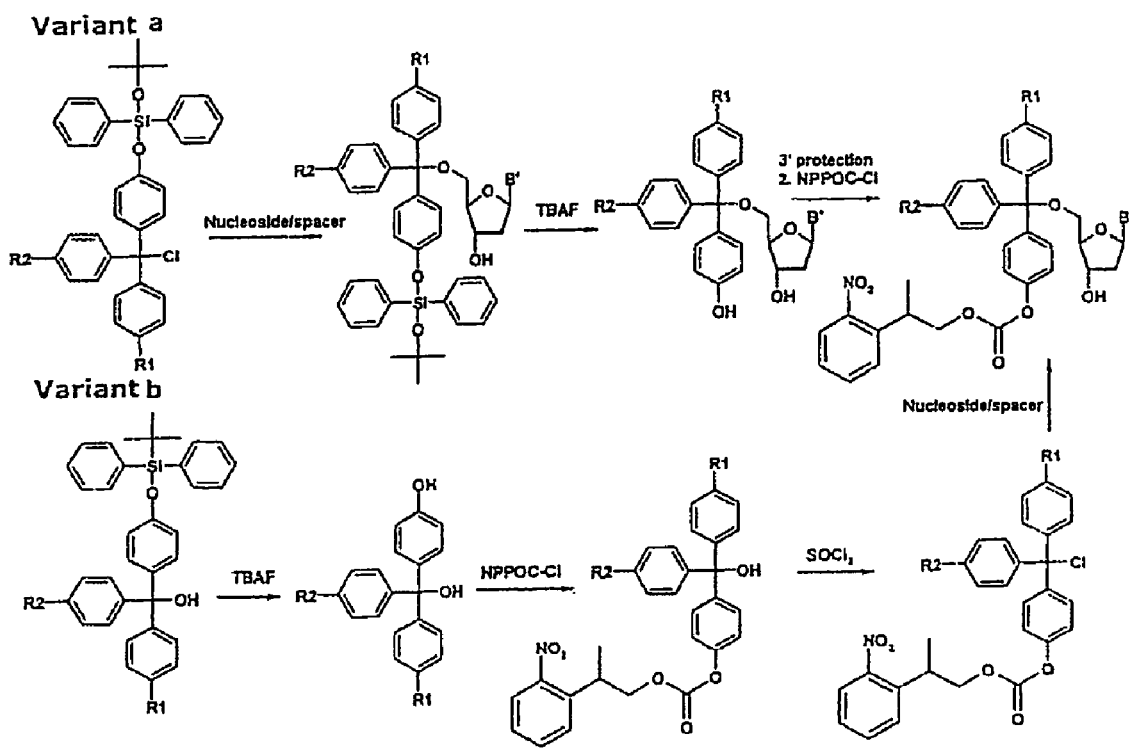
FIG. 4 shows two further variants for the preparation of synthesis building blocks of the invention with two-stage protective groups.
Figure 5:
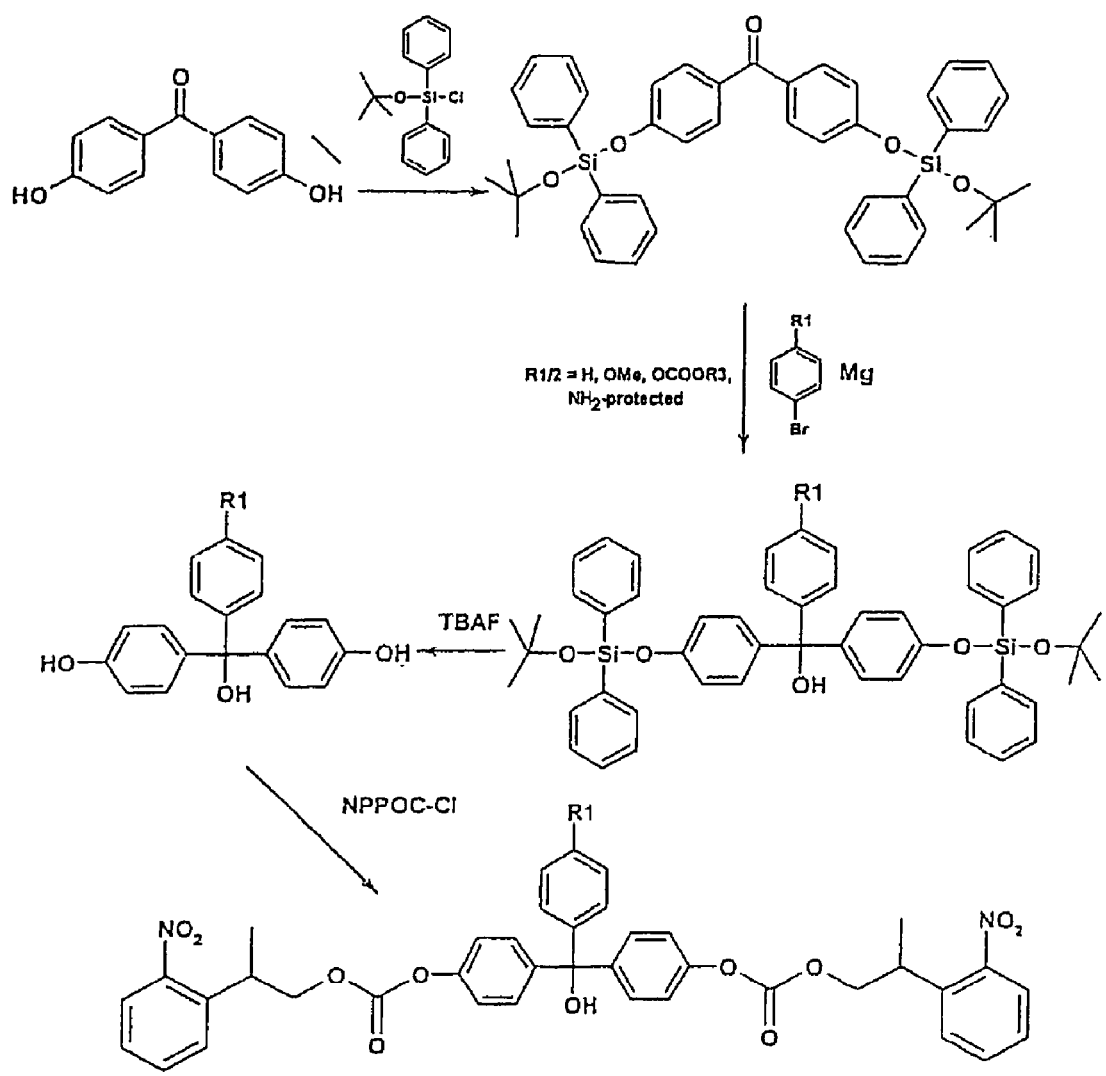
FIG. 5 shows a third variant of the synthesis of two-stage protective groups, with two of the phenyl groups being substituted on the trityl group by a photolabile group.
Figure 6:
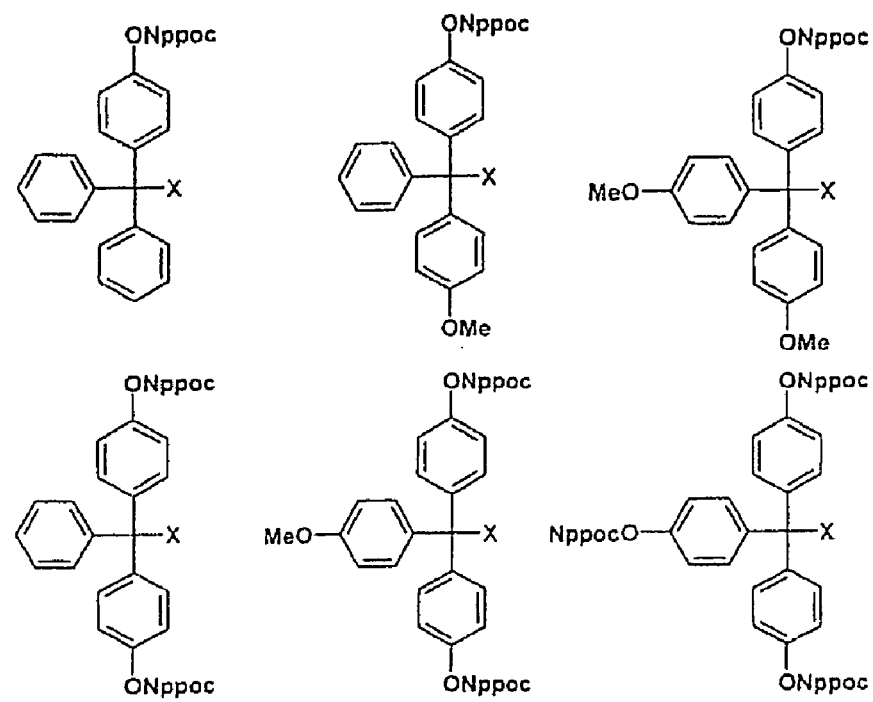
Figure 7:
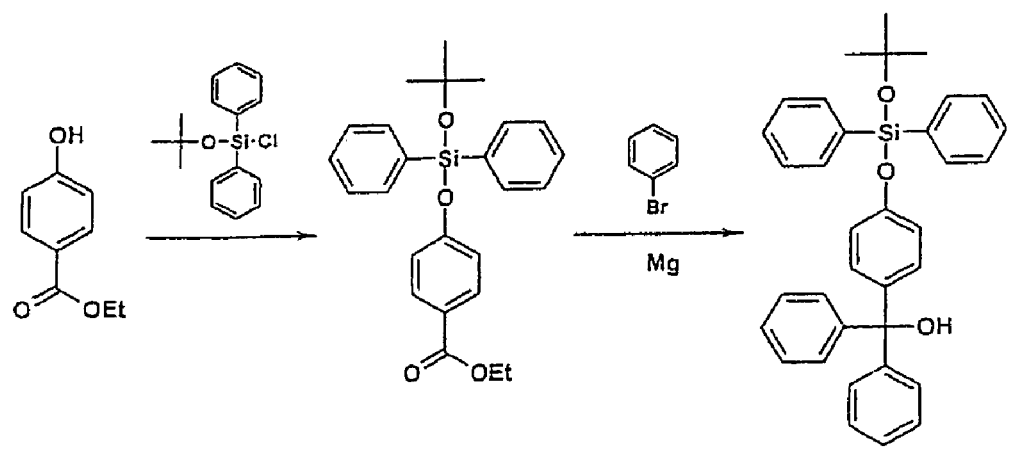

FIG. 6 shows specific embodiments of carbonate derivatives of the two-stage protective group and FIG. 7 shows a process for the synthesis of the S1 protective group. Starting from ethyl 4-hydroxybenzoate and tert-butoxydiphenylchlorosilane in the presence of imidazole it is possible to introduce the silyl group quantitatively. The silyl-derivatized ester is reacted with the Grignard reagent of bromobenzene to give 4-(tert-butoxydiphenylsilyloxy)triphenylcarbinol (S1). In an analogous manner, 4,4'-dimethoxy-4"-(tert-butoxydiphenylsilyloxy)tritylcarbinol (S3, no fig.) is obtained by using bromoanisole.

Figure 8:
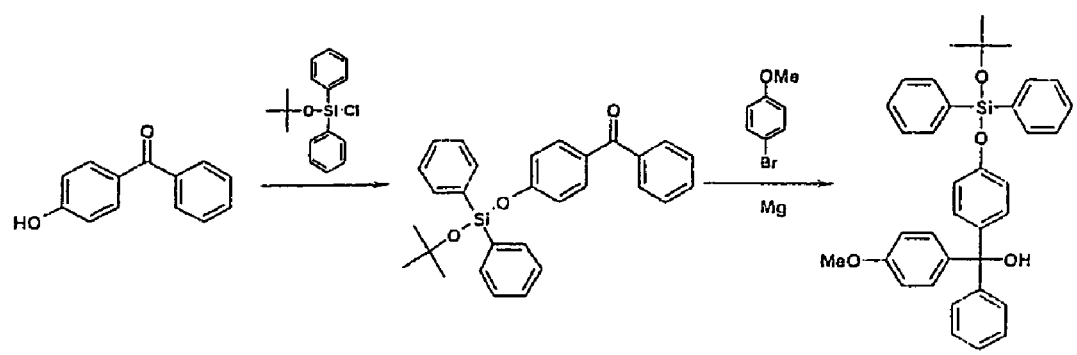
Figure 8:
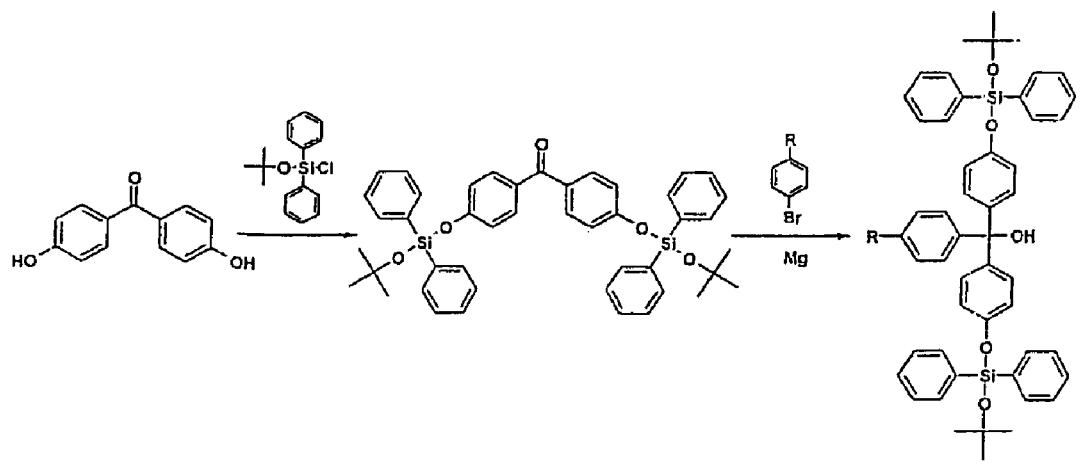

FIG. 8A shows the synthesis of the S2 protective group.

The methoxy silyloxy derivative can be obtained, starting from silyl-protected 4-hydroxybenzophenone which is synthesized in analogy to ethyl hydroxybenzoate in the presence of imidazole, by reaction with the Grignard reagent of bromoanisole to give 4-tert-butoxydiphenylsilyloxytriphenylcarbinol (S2).

FIG. 8B shows a scheme for synthesizing S4/5, R=H or OMe.

The disilyloxy tritylcarbinol derivatives (S4,5) are prepared by reaction of a protected 4,4'-dihydroxybenzophenone which reacts either with bromobenzene (R=H) or with bromoanisole (R=OMe).

Figure 9:
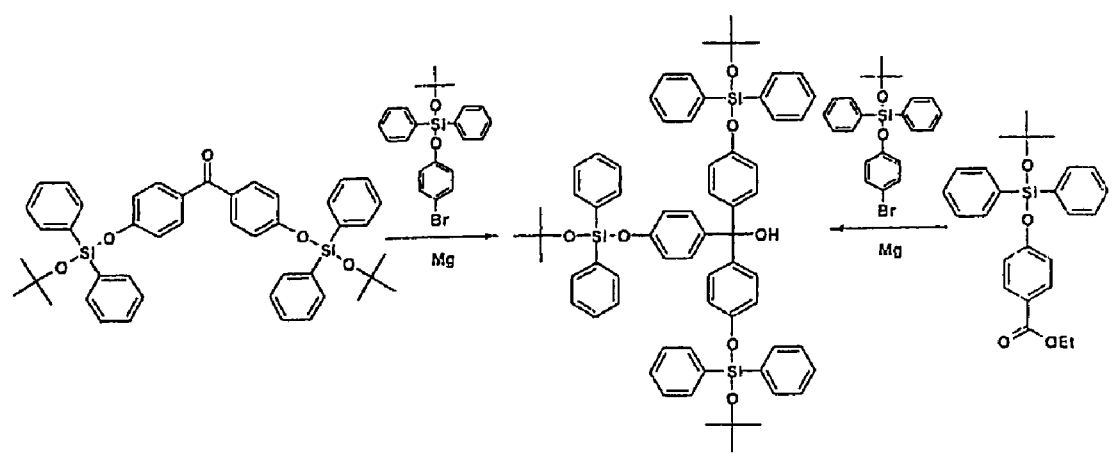

FIG. 9 shows the synthesis of the S6 protective group.

The trisilyloxy tritylcarbinol variant (S6) is prepared either by reacting 4'-silyloxybromobenzene with ethyl 4'-silylbenzoate or by reacting 4,4'-disilyloxybenzophenone and 4'-silyloxybromobenzene.

The tert-butoxydiphenylsilyl group can be eliminated from the silyl-protected compounds by reaction with TBAF for one hour; stopping the reaction by adding pyridine/methanol/water and pyridinium-DOWEX. The derivatives can usually be reacted directly with Nppoc-Cl.

In the subsequent halogenation of carbinols, diverse properties emerge, which are caused by the variation in the electron-attracting and electron-donating substituents in the para position.

Replacement of the alcohol by a halide takes place by the mechanism of 1st order nucleophilic substitution. The result of this is that all processes proceed through a trigonal-planar carbenium ion. The stability of the cation, its structure and the possibility of delocalization of π electrons are crucial for this mechanism. It is additionally stabilized by electron-donating substituents and destabilized by electron-attracting substituents. In this case, the stability of the cation is directly associated with the acid resistance of the protective group. A more stable cation means that the corresponding protective groups are more acid-labile.

A number of standard processes used for halogenating triphenylcarbinol derivatives are described in the literature. Experience with pyrene-substituted dimethoxytritylcarbinols shows that extremely electron-rich compounds can be chlorinated quantitatively with acetyl chloride in cyclohexane within minutes. It emerges that good conversions are achieved with refluxing $SOCl_2$ for selected protective groups with electron-attracting para substituents.

Figure 10:
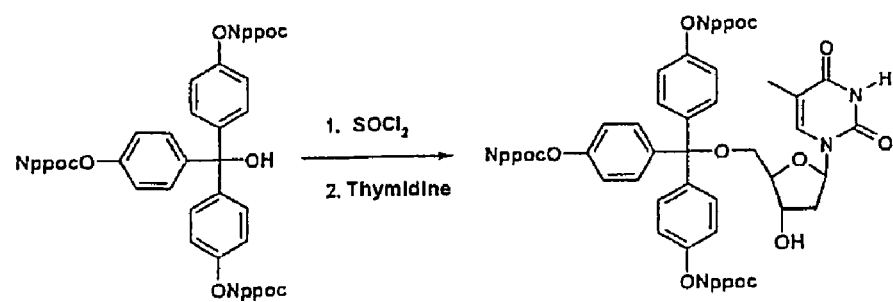

FIG. 10 shows the preparation of protected thymidine derivatives.

Lower yields are obtained for compounds with a plurality of Nppoc groups. It was possible by using refluxing acetyl bromide or $SOBr_2$ to prepare the halogen derivatives in the presence of a plurality of Nppoc substituents on the analytical scale and react them without further workup with thymidine.

Figure 11:
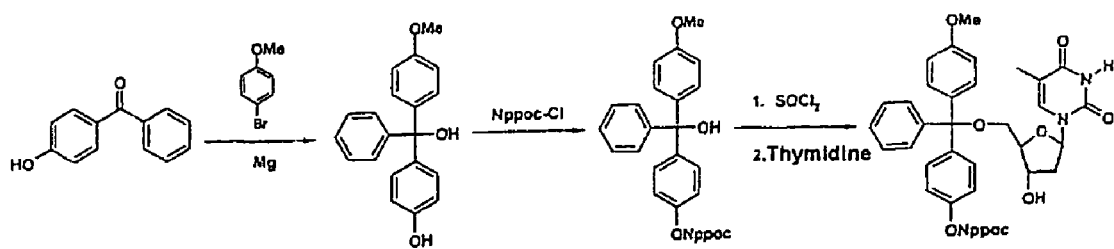

FIG. 11 shows a further process for the synthesis of nucleotides which carry a two-stage protective group.

Figure 12:
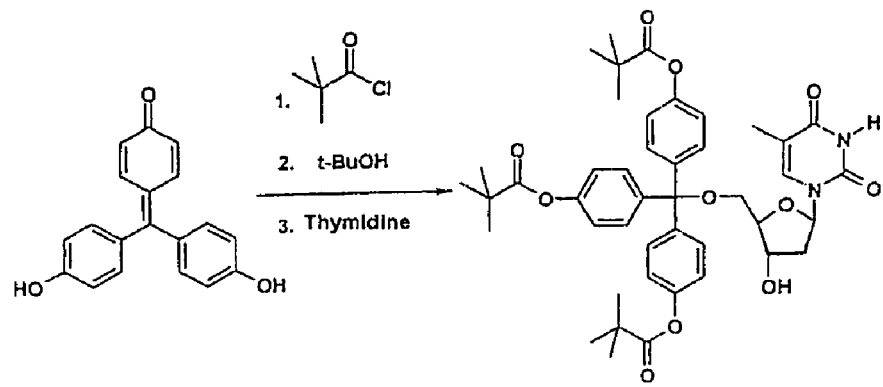
Figure 13:
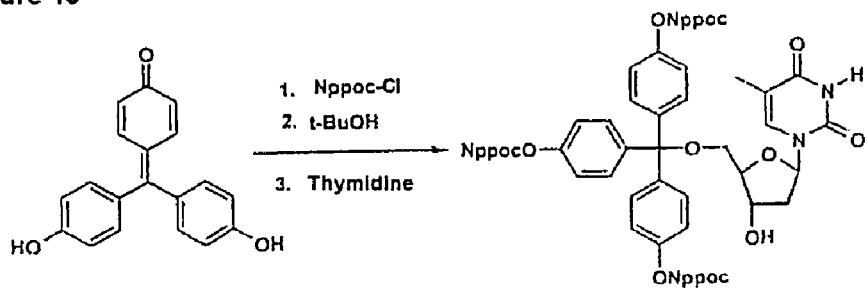

FIG. 12 and FIG. 13 show processes for the preparation of nucleotides which carry a two-stage protective group starting from rosolic acid.

Tri-Nppoc-tritylthymidine is obtained in a one-pot reaction starting from rosolic acid. It is possible to dispense with the use of costly protective groups in this approach. The tripivaloyltrityl derivative was used as model compound for this type of reaction.

The reaction proceeds in a polar aprotic solvent at 50° C. within minutes via an intermediate which then reacts further with the corresponding nucleosides to give the tandem-protected derivatives. The preparation takes place on the preparative scale.

EXAMPLES

Example 1

Synthesis of Tandem Protective Groups 1.1 4-(tert-Butoxydiphenylsilyloxy)triphenylcarbinol (S1)

0.61 g (25.00 mmol, 2.1 eq) of magnesium was suspended in 20 ml of THF in a heat-dried flask under argon. 6.28 g (40.00 mmol, 3.4 eq) of bromobenzene were slowly added dropwise from a dropping funnel with continuous boiling. After the addition was complete, the mixture was heated with an oil bath to 85° C. and stirred for 15 min. The resulting magnesium bromide was allowed to cool to 70° C., and 5.00 g (11.89 mmol, 1 eq) of ethyl 4-tert-butoxydiphenylsilyloxybenzoate dissolved in 20 ml of THF were added dropwise and heated at 85° C. for a further 1.5 h. The mixture was then allowed to cool and stopped with saturated ammonium chloride solution. For the extraction, 500 ml of ethyl acetate were added and extracted 2× with ammonium chloride solution (sat.) and 1× with sodium chloride solution (sat.). The organic phase was dried with sodium sulfate and evaporated. The residue was purified by column chromatography on silica gel 40-63 μm with the eluent ethyl acetate/n-hexane+1% TEA (1:7). 4-(tert-Butoxydiphenylsilyloxy)triphenylcarbinol is obtained as a white powdery solid.

Yield: 5.75 g≈91% of theory.

$R_f$ (ethyl acetate/n-hexane 1:7+1% TEA): 0.19

1.2 4,4'-Dimethoxy-4"-(tert-butoxydiphenylsilyloxy) triphenylcarbinol (S3)

2.78 g (114.14 mmol, 2.4 eq) of magnesium were suspended in 80 ml of THF in a heat-dried flask under argon. 26.68 g (142.67 mmol, 3.0 eq) of bromoanisole were slowly added dropwise from a dropping funnel with continuous boiling. After the addition was complete, the mixture was heated with an oil bath to 85° C. and stirred for 15 min. The resulting magnesium bromide was allowed to cool to 70° C., and 20.00 g (47.56 mmol, 1 eq) of ethyl 4-tert-butoxydiphenylsilyloxybenzoate dissolved in 100 ml of THF were added dropwise and heated at 85° C. for a further 2 h. The mixture was then allowed to cool and stopped with saturated ammonium chloride solution. For the extraction, 500 ml of ethyl acetate were added and extracted 2× with ammonium chloride solution (sat.) and 1× with sodium chloride solution (sat.). The organic phase was dried with sodium sulfate and evaporated. The residue was purified by column chromatography by the step gradient method on silica gel 40-63 μm with the eluent ethyl acetate/n-hexane+1% TEA (1:5 and 1:3). 4,4'-Di-methoxy-4"-(tert-butoxydiphenylsilyloxy) triphenylcarbinol is obtained as a white powdery solid.

Yield: 25.65 g≈97% of theory.

$R_f$ (ethyl acetate/n-hexane 1:3+1% TEA): 0.59

1.3 4-Methoxy-4'-(tert-butoxydiphenylsilyloxy) triphenylcarbinol (S2)

350.64 g (26.51 mmol, 1.2 eq) of magnesium was suspended in 20 ml of THF in a heat-dried flask under argon. 6.20 g (33.14 mmol, 1.5 eq) of bromoanisole were slowly added dropwise from a dropping funnel with continuous boiling. After the addition was complete, the mixture was heated with an oil bath to 85° C. and stirred for 15 min. The resulting magnesium bromide was allowed to cool to 70° C., and 10.00 g (22.09 mmol, 1 eq) of 4-tert-butoxydiphenylsilyloxybenzophenone dissolved in 50 ml of THF were added dropwise and heated at 70° C. for a further 2 h. The mixture was then allowed to cool and stopped with saturated ammonium chloride solution. For the extraction, 250 ml of ethyl acetate were added and extracted 2× with ammonium chloride solution (sat.) and 1× with sodium chloride solution (sat.). The organic phase was dried with sodium sulfate and evaporated. No workup was carried out. 4-Methoxy-4'-(tert-butoxydiphenylsilyloxy)triphenylcarbinol is obtained.

Yield: quantitative reaction $R_f$ (ethyl acetate/n-hexane 1:3+1% TEA): 0.58

1.4 4,4'-di(tert-Butoxydiphenylsilyloxy)triphenylcarbinol (S4)

0.20 g (8.28 mmol, 1.2 eq) of magnesium was suspended in 20 ml of THF in a heat-dried flask under argon. 1.63 g (10.35 mmol, 1.5 eq) of bromobenzene were slowly added dropwise from a dropping funnel with continuous boiling. After the addition was complete, the mixture was heated with an oil bath to 85° C. and stirred for 15 min. The resulting magnesium bromide was allowed to cool to 70° C., and 5.00 g (6.90 mmol, 1 eq) of 4,4'-di-tert-butoxydiphenylsilyloxybenzophenone dissolved in 50 ml of THF were added dropwise and heated at 70° C. for a further 2 h. The mixture was then allowed to cool and stopped with saturated ammonium chloride solution. For the extraction, 250 ml of ethyl acetate were added and extracted 2× with ammonium chloride solution (sat.) and 1× with sodium chloride solution (sat.). The organic phase was dried with sodium sulfate and evaporated. The residue was purified by column chromatography on silica gel 40-63 μm with the eluent ethyl acetate/n-hexane+1% TEA (1:7). 4,4'-di-(tert-Butoxydiphenylsilyloxy) triphenylcarbinol is obtained as a white powdery solid.

Yield: 3.00 g≈54% of theory.

$R_f$ (ethyl acetate/n-hexane 1:7+1% TEA): 0.27

1.5 4,4'-di(tert-Butoxydiphenylsilyloxy)-4"-methoxytriphenylcarbinol (S5)

0.20 g (8.28 mmol, 1.2 eq) of magnesium was suspended in 20 ml of THF in a heat-dried flask under argon. 1.94 g (10.35 mmol, 1.5 eq) of bromoanisole were slowly added dropwise from a dropping funnel with continuous boiling. After the addition was complete, the mixture was heated with an oil bath to 85° C. and stirred for 15 min. The resulting magnesium bromide was allowed to cool to 70° C., and 5.00 g (6.90 mmol, 1 eq) of 4,4'-di-tert-butoxydiphenylsilyloxybenzophenone dissolved in 50 ml of THF were added dropwise and heated at 70° C. for a further 2 h. The mixture was then allowed to cool and stopped with saturated ammonium chloride solution. For the extraction, 250 ml of ethyl acetate were added and extracted 2× with ammonium chloride solution (sat.) and 1× with sodium chloride solution (sat.). The organic phase was dried with sodium sulfate and evaporated. The residue was purified by column chromatography on silica gel 40-63 μm with the eluent ethyl acetate/n-hexane+1% TEA (1:5). 4,4'-di-(tert-Butoxydiphenylsilyloxy)-4"-methoxytriphenylcarbinol is obtained as a white powdery solid.

Yield: 3.00 g≈52% of theory.

$R_f$ (ethyl acetate/n-hexane 1:5+1% TEA): 0.26

1.6 4,4',4"-tri(tert-Butoxydiphenylsilyloxy)triphenylcarbinol (S6)

0.41 g (16.87 mmol, 1.2 eq) of magnesium was suspended in 20 ml of THF in a heat-dried flask under argon. 18.90 g (20.86 mmol, 1.5 eq) of 4-tert-butoxydiphenylsilyloxybromobenzene were slowly added dropwise from a dropping funnel with continuous boiling. After the addition was complete, the mixture was heated with an oil bath to 85° C. and stirred for 15 min. The resulting magnesium bromide was allowed to cool to 70° C., and 1 eq 10.10 g (13.97 mmol) of 4,4'-di-tert-butoxydiphenylsilyloxybenzophenone dissolved in 50 ml of THF were added dropwise and heated at 70° C. for a further 2 h. The mixture was then allowed to cool and stopped with saturated ammonium chloride solution. For the extraction, 250 ml of ethyl acetate were added and extracted 2× with ammonium chloride solution (sat.) and 1× with sodium chloride solution (sat.). The organic phase was dried with sodium sulfate and evaporated. The residue was purified by column chromatography on silica gel 40-63 μm with the eluent ethyl acetate/n-hexane+1% TEA (1:10). 4,4',4"-tri-(tert-Butoxydiphenylsilyloxy)triphenylcarbinol is obtained as a white powdery solid.

Yield: 10.20 g≈68% of theory.

$R_f$ (ethyl acetate/n-hexane 1:10+1% TEA): 0.23

1.7 4-(2-[2-Nitrophenyl]propyloxycarbonyloxy) triphenylcarbinol 6.00 ml (6.00 mmol, 1.1 eq) of 1M TBAF solution were added dropwise to 2.87 g (5.41 mmol, 1 eq) of 4-tert-butoxydiphenylsilyloxytriphenylcarbinol dissolved in 20 ml of THF and stirred at room temperature (RT) for 1 h. 5 ml of pyridine/MeOH/water (3:1:1) and pyridinium-Dowex were added to stop the reaction. After 30 min, filtration and washing with pyridine were carried out. The solution was then coevaporated with pyridine several times. 1.97 g (8.12 mmol, 1.5 eq) of Nppoc-Cl dissolved in 10 ml of methylene chloride were added dropwise to the mixture dissolved in 60 ml of pyridine/methylene chloride (2:1) and stirred at RT for 16 h. The mixture was then concentrated and taken up in methylene chloride and extracted 2× with sodium bicarbonate solution (1N) and 1× with sodium chloride solution (sat.). The organic phase was dried and evaporated. The residue was purified by column chromatography on silica gel 40-63 µm with the eluent ethyl acetate/n-hexane+1% TEA (1:2). 4-Nppoc-triphenylcarbinol is obtained as a solid white foam.

Yield: 2.16 g≈83% of theory.

$R_f$ (ethyl acetate/n-hexane 1:1+1% TEA): 0.68

1.8 4-Methoxy-4'-(2-[2-nitrophenyl]propyloxycarbonyloxy)triphenylcarbinol (S2)

15.70 ml (15.70 mmol, 1.1 eq) of 1M TBAF solution were added dropwise to 8.00 g (14.27 mmol, 1 eq) of 4-methoxy-4'-tert-butoxydiphenylsilyloxytriphenylcarbinol dissolved in 50 ml of THF and stirred at RT for 1 h. The reaction was stopped by adding 20 ml of pyridine/MeOH/water (3:1:1) and pyridinium-Dowex. After 30 min, filtration and washing with pyridine were carried out. The solution was then coevaporated with pyridine several times. 6.50 g (26.75 mmol, 1.9 eq) of Nppoc-Cl dissolved in 15 ml of methylene chloride were added dropwise to the mixture dissolved in 60 ml of pyridine/methylene chloride (2:1) and stirred at RT for 16 h. The mixture was then concentrated and dissolved in methylene chloride, and extracted 2× with sodium bicarbonate solution (1N) and 1× with sodium chloride solution (sat.). The organic phase was dried and evaporated. The residue was purified by column chromatography by the step gradient method on silica gel 40-63 µm with the eluent ethyl acetate/n-hexane+1% TEA (1:3 and 1:2). 4-Methoxy-4'-Nppoc-triphenylcarbinol is obtained as a solid white foam.

Yield: 5.5 g≈75% of theory.

$R_f$ (ethyl acetate/n-hexane 1:1+1% TEA): 0.54

$^{13}$C-NMR: (125.75 MHz, CDCl$_3$, TMS): δ=17.70 (CH3-nppoc), 33.19 (CH-nppoc), 55.16 (CH3-O), 72.09 (CH2-nppoc), 81.31 (C-trityl), 113.23 (C-3,5-methoxyphenyl(trityl)), 120.04 (C-3,5-nppocphenyl(trityl)), 124.36 (C-3-phenyl-nppoc), 126.83 (C-4-phenyl(trityl)), 127.71 (C-2,6-phenyl(trityl)), 127.91 (C-6-phenyl-nppoc), 128.28 (C-4-phenyl-nppoc), 129.03 (C-3,5-phenyl (trityl)), 129.11 (C-2,6-nppocphenyl(trityl)), 129.35 (C-2,6-methoxyphenyl (trityl)), 132.76 (C-5-phenyl-nppoc), 136.63 (C-1-phenyl-nppoc), 138.88 (C-1-methoxyphenyl(trityl)), 144.87 (C-1-nppocphenyl-(trityl)), 146.75 (C-1-phenyl(trityl)), 149.93 (C-2-phenyl-nppoc), 150.18 (O(CO)O), 153.35 (C-4-nppoc-phenyl(trityl)), 158.71 ppm (C-4-methoxyphenyl (trityl)).

1.9 4,4'-Dimethoxy-4"-(2-[2-nitrophenyl]propyloxycarbonyloxy)triphenylcarbinol (S3)

8.00 ml (8.00 mmol, 1.1 eq) of 1M TBAF solution were added dropwise to 4.00 g (7.23 mmol, 1 eq) of 4,4'-dimethoxy-4"-tert-butoxydiphenylsilyloxytriphenylcarbinol dissolved in 20 ml of THF and stirred at RT for 1 h. The reaction was stopped by adding 10 ml of pyridine/MeOH/water (3:1:1) and pyridinium-Dowex. After 30 min, filtration, washing with pyridine and concentration were carried out. The residue was purified by column chromatography by the step gradient method on silica gel 40-63 µm, eluent ethyl acetate/n-hexane+1% TEA (1:3 and 1:1). 0.40 g (1.70 mmol, 1.4 eq) of Nppoc-Cl dissolved in 5 ml of methylene chloride was added dropwise to 0.40 g (1.25 mmol) of the resulting 4,4'-dimethoxy-4"-hydroxytriphenylcarbinol dissolved in 30 ml of pyridine/methylene chloride (2:1). The mixture was stirred at RT for 16 h. It was then concentrated, dissolved in methylene chloride and extracted 2× with sodium bicarbonate solution (1N) and 1× with sodium chloride solution (sat.). The organic phase was dried and evaporated. The residue was purified by column chromatography on silica gel 40-63 µm with the eluent ethyl acetate/n-hexane+1% TEA (1:3). 4,4'-Dimethoxy-4"-Nppoc-triphenylcarbinol is obtained as a solid white foam.

Yield: 0.57 g≈86% of theory.

$R_f$ (ethyl acetate/n-hexane 1:1+1% TEA): 0.59

1.10 4,4'-di(2-[2-Nitrophenyl]propyloxycarbonyloxy)triphenylcarbinol (S4)

5.28 ml (5.28 mmol, 2.2 eq) of 1M TBAF solution were added dropwise to 2.00 g (2.40 mmol, 1 eq) of 4,4'-di-tert-butoxydiphenylsilyloxytriphenylcarbinol dissolved in 30 ml of THF and stirred at RT for 1 h. The reaction was stopped by adding 20 ml of pyridine/MeOH/water (3:1:1) and pyridinium-Dowex. After 30 min, filtration and washing with pyridine were carried out. The solution was then coevaporated with pyridine several times. 2.19 g (9.00 mmol, 3.7 eq) of Nppoc-Cl dissolved in 10 ml of methylene chloride were added dropwise to the mixture dissolved in 60 ml of pyridine/methylene chloride (2:1) and stirred at RT for 16 h. The mixture was then concentrated, dissolved in methylene chloride and extracted 2× with sodium bicarbonate solution (1N) and 1× with sodium chloride solution (sat.). The organic phase was dried and evaporated. The residue was purified by column chromatography on silica gel 40-63 µm with the eluent ethyl acetate/n-hexane+1% TEA (1:1). 4,4'-di-Nppoc-triphenylcarbinol is obtained as a solid white foam.

Yield: 0.75 g≈40.9% of theory.

$R_f$ (ethyl acetate/n-hexane 1:1+1% TEA): 0.55

1.11 4-Methoxy-4',4"-di(2-[2-nitrophenyl]propyloxycarbonyloxy)triphenylcarbinol (S5)

20.77 ml (20.77 mmol, 2.2 eq) of 1M TBAF solution were added dropwise to 7.85 g (9.44 mmol, 1 eq) of 4-methoxy-4',4"-di-tert-butoxydiphenylsilyloxytriphenylcarbinol dissolved in 50 ml of THF and stirred at RT for 1 h. The reaction was stopped by adding 20 ml of pyridine/MeOH/water (3:1:1) and pyridinium-Dowex. After 30 min, filtration and washing with pyridine were carried out. The solution was then coevaporated with pyridine several times. 6.10 g (25.03 mmol, 2.6 eq) of Nppoc-Cl dissolved in 10 ml of methylene chloride were added dropwise to the mixture dissolved in 60 ml of pyridine/methylene chloride (2:1) and stirred at RT for 16 h. The mixture was then concentrated, dissolved in methylene chloride and extracted 2× with sodium bicarbonate solution (1N) and 1× with sodium chloride solution (sat.). The organic phase was dried and evaporated. The residue was purified by column chromatography by the step gradient method on silica gel 40-63 µm with the eluent ethyl acetate/n-hexane+1% TEA (1:2, 2:3 to 1:1). 4-Methoxy-4',4"-di-Nppoc-triphenylcarbinol is obtained as a solid white foam.

Yield: 3.0 g≈43% of theory.

$R_f$ (ethyl acetate/n-hexane 1:1+1% TEA): 0.65

1.12 4,4',4''-tri(2-[2-Nitrophenyl]propyloxycarbonyloxy)triphenylcarbinol (S6)

31.45 ml (31.45 mmol, 3.3 eq) of 1M TBAF solution were added dropwise to 10.20 g (9.53 mmol, 1 eq) of 4,4',4''-tri-tert-butoxydiphenylsilyloxytriphenylcarbinol dissolved in 200 ml of THF and stirred at RT for 1 h. The reaction was stopped by adding 20 ml of pyridine/MeOH/water (3:1:1) and pyridinium-Dowex. After 30 min, filtration and washing with pyridine were carried out. The solution was then coevaporated with pyridine several times. 9.29 g (38.12 mmol, 4.0 eq) of Nppoc-Cl dissolved in 20 ml of methylene chloride were added dropwise to the mixture dissolved in 120 ml of pyridine/methylene chloride (2:1) and stirred at RT for 16 h. The mixture was then concentrated, dissolved in methylene chloride and extracted 2× with sodium bicarbonate solution (1N) and 1× with sodium chloride solution (sat.). The organic phase was dried and evaporated. The residue was purified by column chromatography by the step gradient method on silica gel 40-63 μm with the eluent ethyl acetate/n-hexane+1% TEA (1:2, to 1:1). 4,4',4''-tri-Nppoc-triphenylcarbinol is obtained as a solid white foam.

Yield: 3.9 g≈44% of theory.

$R_f$ (ethyl acetate/n-hexane 1:1+1% TEA): 0.49

$^{13}$C-NMR: (125.75 MHz, CDCl$_3$, TMS): δ=17.68 (CH3-nppoc), 33.17 (CH-nppoc), 72.14 (CH2-nppoc), 80.89 (C-trityl), 120.31 (C-3,3',3'',5,5',5''-trityl), 124.35 (C-3-phenyl-nppoc), 127.83 (C-6-phenyl-nppoc), 128.27 (C-4-phenyl-nppoc), 128.99 (C-2,2',2'',6,6',6''-trityl), 132.77 (C-5-phenyl-nppoc), 136.62 (C-1-phenyl-nppoc), 144.09 (C-1,1',1''-trityl), 150.14 (O(CO)O), 150.17 (C-2-phenyl-nppoc), 153.36 ppm (C-4,4',4''-trityl).

MS (TOF, ES+): 952.29 [M+Na], 968.25 [M+K].

MS (TOF, ES−): 928.42 [M−H], 694.37 [M−Cl].

C$_{49}$H$_{43}$N$_3$O$_{16}$: 929.90

1.13 Halogenation and Etherification to Give 5'-O-Nppoc-triphenylmethylthymidine Derivatives 1 eq of the triphenylcarbinol derivative were heated with 100 eq of thionyl chloride at 90° C. for 3 h. Methylene chloride was then added and heated was continued for 2 h. The mixture was then concentrated with cyclohexane 3×. The resulting triphenylmethyl chloride derivative was dissolved in methylene chloride and, under protective gas, 2 eq of thymidine dissolved in pyridine and methylene chloride were added dropwise. After stirring at RT for 16 h, the reaction was stopped by adding ethanol. The mixture was then concentrated, dissolved in methylene chloride and extracted 2× with sodium bicarbonate solution (1N) and 1× with saturated sodium chloride solution. The organic phase was dried and evaporated. The residue was purified by column chromatography on silica gel 40-63 μm. Mobile phases and yields are to be found in table 1 below:

TABLE 1

| Substance | Boiling time SOCl$_2$ | $R_f$: eluent + 1% TEA | Yield |
|---|---|---|---|
| 5'-O-(4-Nppoc-trityl)-thymidine | 2 + 3 h | (CH$_2$Cl$_2$ + 5% MeOH) 0.26 | 95% |
| 5'-O-(4-Methoxy-4'-Nppoc-trityl)thymidine | 3 + 2 h | (EA/Hex 2:1) 0.18 | 50% |
| 5'-O-(4,4'-dimethoxy-4''-Nppoc-trityl)thymidine | 2 + 3 h | (CH$_2$Cl$_2$ + 5% MeOH) 0.30 | 83% |
| 5'-O-(4,4'-DiNppoc-trityl)thymidine | 4 + 1 h | (EA/Hex 3:1) 0.34 | 26% |
| 5'-O-(4-methoxy-4',4''-diNppoc-trityl)-thymidine | 4 + 1 h | (EA/Hex 2:1) 0.21 | 44% |
| 5'-O-(4,4'4''-triNppoc-trity)lthymidine | 4 + 1 h | (EA/Hex 3:1) 0.25 | 13% |

The 5'-triphenylmethylthymidine derivatives are obtained as a solid white foam in yields between 13-95% of theory.

NMR Data for 5'-O-(4-methoxy-4'-(2-[2-nitrophenyl)propyloxycarbonyloxy)trityl]thymidine $^{13}$C-NMR: (125.75 MHz, CDCl$_3$, TMS): δ=11.78 (5-CH3) 17.60 (CH3-nppoc), 33.10 (CH-nppoc), 40.72 (C-2'), 55.15 (O-CH3), 63.67 (C-5'), 70.95 (C-3'), 72.11 (CH2-nppoc), 84.65 (C-4'), 85.03 (C-1'), 86.64 (C-trityl), 111.20 (C-5), 113.25 (C-3,5-methoxyphenyl (trityl)), 120.35 (C-3,5-nppocphenyl(trityl)), 124.27 (C-3-phenyl-nppoc), 127.27 (C-4-phenyl(trityl)), 127.69 (C-6-phenyl-nppoc), 127.79 (C-2,6-phenyl(trityl)), 128.19 (C-4-phenyl-nppoc), 128.98 (C-4-phenyl-nppoc), 129.07 (C-2,6-nppocphenyl(trityl)), 134.35 (C-1-methoxyphenyl(trityl)), 135.54 (C-6), 136.52 (C-1-phenyl-nppoc), 141.60 (C-1-nppocphenyl(trityl)), 144.91 (C-1-phenyl(trityl)), 149.80 (C-2-phenyl-nppoc), 150.08 (O(CO)O), 150.61 (C-2), 153.31 (C-4-nppocphenyl (trityl)), 158.74 (C-4-methoxyphenyl(trityl)), 164.17 ppm (C-4).

1.14 4-Methoxy-4'-(2-[2-nitrophenyl]propyloxycarbonyloxy)triphenylcarbinol (S2)

For synthesis without protective groups, 0.50 g (20.60 mmol, 1.2 eq) of magnesium was suspended in 20 ml of THF in a heat-dried flask under argon. 3.2 ml (25.70 mmol, 1.5 eq) of bromoanisole were slowly added dropwise from a dropping funnel while boiling continuously. After the addition was complete, the mixture was heated to 85° C. with an oil bath and stirred for 15 minutes. The resulting magnesium bromide was allowed to cool to 70° C., and 3.40 g (17.17 mmol, 1 eq) of 4-hydroxybenzophenone dissolved in 50 ml of THF were added dropwise and stirred at 70° C. for a further 2 h. The mixture was then allowed to cool and the reaction was stopped with saturated ammonium chloride solution. For extraction, 250 ml of ethyl acetate were added and extracted 2× with ammonium chloride solution (sat.) and 1× with sodium chloride solution (sat.). The organic phase was dried with sodium sulfate and evaporated. The workup was dispensed with, and coevaporation with pyridine was carried out several times.

11.00 g (45.00 mmol) of Nppoc-Cl dissolved in 15 ml of methylene chloride were added dropwise to the mixture dissolved in 40 ml of pyridine/methylene chloride (1:1) and stirred at RT for 16 h. The mixture was then concentrated, dissolved in methylene chloride and extracted 2× with sodium bicarbonate solution (1N) and 1× with sodium chloride solution (sat.). The organic phase was dried and evaporated. The residue was purified by column chromatography by the step gradient method on silica gel 40-63 μm, eluent ethyl acetate/n-hexane+1% TEA (1:3 and 1:2). 4-Methoxy-4'-Nppoc-triphenylcarbinol is obtained as a solid white foam.

Yield: 3.7 g≈42% of theory.
R$_f$ (ethyl acetate/n-hexane 1:1+1% TEA): 0.54

1.15 5'-O-(4,40,4"-tripivaloyltriphenylmethyl)thymidine from rosolic acid 10 ml (9.8 mmol, 4.7 eq) of pivaloyl acid chloride were added dropwise to 5 g (17.22 mmol) of p-rosolic acid dissolved in 75 ml of pyridine and 2.5 ml of 2,6-lutidine. The mixture was then stirred at 70° C. for 80 min. On cooling, crystals formed and were isolated and washed with pyridine. 1 g (1.73 mmol) of the crystals were dissolved in 25 ml of methylene chloride and reacted with DMAP catalysis (20 mg, 0.17 mmol) with 20 ml of 2,6-lutidine and 220 mg (0.86 mmol) of thymidine. The mixture was then concentrated, dissolved in methylene chloride and extracted 2× with sodium bicarbonate solution (1N) and 1× with sodium chloride solution (sat.). The organic phase was dried and evaporated. The residue was purified by column chromatography by the step gradient method on silica gel 40-63 µm, eluent ethyl acetate/n-hexane+1% TEA (1:3, 1:2). 5'-O-(4,4',4"-tripivaloyltriphenylmethyl)thymidine is obtained as a solid white foam.

Yield: 0.18 g≈13.15% of theory.

$^{13}$C-NMR: (125.75 MHz, CDCl$_3$, TMS): δ=12.11 (5-CH3) 27.02 (CH3-piv), 38.93 (C-piv), 41.02 (C-2'), 63.92 (C-5'), 70.33 (C-3'), 84.53 (C-4'), 85.92 (C-1'), 86.20 (C-trityl), 110.82 (C-5), 120.97 (C-3,3',3",5,5',5"-trityl), 129.59 (C-2,2',2",6,6',6"-trityl), 135.09 (C-6), 140.47 (C-1,1',1"-trityl) 151.00 (C-2), 154.21 (C-4,4',4"-trityl), 164.10 (C-4), 176.78 ppm (C=O-piv).

1.16 5'-O-(4,4',4"-tri(2-[2-Nitrophenyl]propyloxycarbonyloxy)triphenylmethyl)deoxythymidine from rosolic acid 10 g (34.44 mmol) of p-rosolic acid dissolved in 120 ml of pyridine and 30 ml of 2,6-lutidine was heated to 50° C., and 44 g (178.28 mmol) of Nppoc-Cl were added dropwise. After reaction at 50° C. for 16 h, excess chloride was quenched by adding t-buthanol. The reaction was checked by TLC (R$_f$ (ethyl acetate/n-hexane 1:1+1% TEA): 0.35). After reaction for a further 30 min, 8.2 g of thymidine and 750 mg of DMAP were added at a temperature of 45° C. After stirring for 16 h, the mixture was concentrated, dissolved in methylene chloride and extracted 2× with sodium bicarbonate solution (1N) and 1× with sodium chloride solution (sat.). The organic phase was dried and evaporated. The residue was purified by column chromatography on silica gel 40-63 µm, eluent ethyl acetate/n-hexane+1% TEA (3:1). 5'-O-(4,4',4"-tri-(2-[2-Nitrophenyl]propyloxycarbonyloxy)triphenylmethyl) deoxythymidine is obtained as a solid white foam.

Yield: 10 g≈25% of theory.
R$_f$ (ethyl acetate/n-hexane 3:1+1% TEA): 0.25

$^{13}$C-NMR: (125.75 MHz, CDCl$_3$, TMS): δ=12.00 (5-CH3) 17.59 (CH3-nppoc), 33.06 (CH-nppoc), 40.50 (C-2'), 63.74 (C-5'), 71.48 (C-3'), 72.14 (CH2-nppoc), 84.55 (C-4'), 85.52 (C-1'), 86.16 (C-trityl), 111.13 (C-5), 120.58 (C-3,3',3",5,5',5"-trityl), 124.26 (C-3-phenyl-nppoc), 127.63 (C-6-phenyl-nppoc), 128.19 (C-4-phenyl-nppoc), 129.58 (C-2,2',2",6,6',6"-trityl), 135.29 (C-6), 136.47 (C-1-phenyl-nppoc), 140.53 (C-1,1',1"-trityl), 150.09 (C-2-phenyl-nppoc), 150.34 (O(CO)O), 150.34 (C-2), 153.13 (C-4,4',4"-trityl), 163.73 ppm (C-4).

MS (TOF, ES$^+$): 1 175.89 [M+Na], 1 191.83 [M+K].
MS (TOF, ES$^-$): 1 152.87 [M−H].
C$_{59}$H$_{55}$N$_5$O$_{20}$: 1 154.12

1.17 5'-O-(4,4',4"-tri(2-[2-Nitrophenyl]propyloxycarbonyloxy) triphenylmethyl)-N$^4$-isobutryldeoxycytidine 2.8 g (9.64 mmol) of p-rosolic acid dissolved in 20 ml of pyridine and 20 ml of 2,6-lutidine were heated to 50° C., and 14.0 g (56.72 mmol) of Nppoc-Cl were added dropwise. After 30 min, excess chloride was quenched by adding t-butanol. The reaction was checked by TLC (R$_f$ (methylene chloride/methanol 5%+1% TEA): 0.36). After reaction at a temperature of 45° C. for a further 30 min, 3.80 g of N$^4$-isobutryldeoxycytidine and 250 mg of DMAP dissolved in 30 ml of DMF were added. After 36 h, the mixture was concentrated, dissolved in methylene chloride and extracted 2× with sodium bicarbonate solution (1N) and 1× with sodium chloride solution (sat.). The organic phase was dried and evaporated. The residue was purified by column chromatography on silica gel 40-63 µm, eluent ethyl acetate/n-hexane+1% TEA (3:1). 5'-O-(4,4',4"-tri(2-[2-Nitrophenyl]propyloxy-carbonyloxy)triphenylmethyl)-N$^4$-isobutryldeoxycytidine is obtained as a solid white foam.

Yield: 2.6 g≈16.8% of theory.
R$_f$ (ethyl acetate/n-hexane 3:1+1% TEA): 0.25

$^{13}$C-NMR: (125.75 MHz, CDCl$_3$, TMS): δ=17.61 (CH3-nppoc), 18.89 (CH3-ibu), 33.10 (CH-nppoc), 36.10 (CH-ibu), 41.69 (C-2'), 63.39 (C-5'), 70.67 (C-3'), 72.10 (CH2-nppoc), 85.90 (C-4'), 86.18 (C-trityl), 87.06 (C-1'), 96.45 (C-5), 120.60 (C-3,3',3",5,5',5"-trityl), 124.27 (C-3-phenyl-nppoc), 127.62 (C-6-phenyl-nppoc), 128.21 (C-4-phenyl-nppoc), 129.55 (C-2,2',2",6,6',6"-trityl), 132.72 (C-5-phenyl-nppoc), 136.50 (C-1-phenyl-nppoc), 140.50 (C-1,1',1"-trityl), 143.85 (C-6), 150.08 (O(CO)O), 150.08 (C-2-phenyl-nppoc), 153.15 (C-4,4',4"-trityl), 155.32 (C-2), 162.32 (C-4), 176.91 ppm (C=O-ibu).

MS (TOF, ES$^+$): 1 209.48 [M+H], 1 231.48 [M+Na].
MS (TOF, ES$^-$): 1 209.48 [M−H].
C$_{62}$H$_{60}$N$_6$H$_{20}$: 1 209.20

1.18 5'-O-(4,4',4"-tri(2-[2-Nitrophenyl]propyloxycarbonyloxy)triphenylmethyl)-N$^6$-pivaloyldeoxyadenosine 2.8 g (9.64 mmol) of p-rosolic acid dissolved in 20 ml of pyridine and 20 ml of 2,6-lutidine were heated to 50° C., and 14.0 g (56.72 mmol) of Nppoc-Cl were added dropwise. After 30 min, excess chloride was quenched by adding t-butanol. The reaction was checked by TLC (R$_f$ (methylene chloride/methanol 5%+1% TEA): 0.36). After reaction for a further 30 min at a temperature of 45° C., 5.7 g of N$^6$-pivaloyldeoxyadenosine and 250 mg of DMAP dissolved in 30 ml of DMF were added. After 36 h, the mixture was concentrated, dissolved in methylene chloride and extracted 2× with sodium bicarbonate solution (1N) and 1× with sodium chloride solution (sat.). The organic phase was dried and evaporated. The residue was purified by column chromatography on silica gel 40-63 µm, eluent ethyl acetate/n-hexane+1% TEA (3:1). 5'-O-(4,4',4"-tri(2-[2-Nitrophenyl]propyloxy-carbonyloxy)triphenylmethyl)-N$^6$-pivaloyld is obtained as a solid white foam.

Yield: 1.3 g≈6.8% of theory.

$^{13}$C-NMR: (125.75 MHz, CDCl$_3$, TMS): δ=17.56 (CH3-nppoc) 27.40 (CH3-piv), 33.04 (CH-nppoc), 39.69 (C-2'), 40.32 (C-piv), 63.73 (C-5'), 71.48 (C-3'), 72.35 (CH2-nppoc) 84.45 (C-4'), 85.82 (C-trityl), 85.90 (C-1'), 120.39 (C-3,3',3",5,5',5"-trityl), 122.61 (C-5), 124.21 (C-3-phenyl-nppoc), 127.58 (C-6-phenyl-nppoc), 128.17 (C-4-phenyl-nppoc), 129.51 (C-2,2',2",6,6',6"-trityl), 132.59 (C-5-phenyl-nppoc), 136.67 (C-1-phenyl-nppoc), 140.68 (C-1,1',1''-trityl), 141.32 (C-8), 149.90 (C-4), 149.93 (C-2-phenyl-nppoc), 150.03 (O(CO)O), 151.02 (C-6), 152.30 (C-2), 153.10 (C-4,4',4''-trityl), 175.67 ppm (C=O-piv).

MS (TOF, ES$^+$): 1 247.49 [M+H], 1 270.48 [M+Na].
MS (TOF, ES$^-$): 1 245.46 [M−H].
$C_{64}H_{63}N_8O_{19}$: 1 247.25

1.19 5'-O-(4,4',4''-tri(2-[2-Nitrophenyl]propyloxycarbonyloxy)triphenylmethyl)-N-2-isobutryldeoxyguanosine 4.0 g (13.8 mmol) of p-rosolic acid dissolved in 50 ml of pyridine and 30 ml of 2,6-lutidine were heated to 50° C., and 18.0 g (73.9 mmol) of Nppoc-Cl were added dropwise. After 16 h, excess chloride was quenched by adding t-butanol. The reaction was checked by TLC ($R_f$ (ethyl acetate/n-hexane 1:1+1% TEA): 0.36). After reaction for a further 30 min at a temperature of 40° C., 4.60 g of $N^2$-isobutryldeoxyguanosine and 250 mg of DMAP dissolved in 30 ml of DMF were added. After 36 h, the mixture was concentrated, dissolved in methylene chloride and extracted 2× with sodium bicarbonate solution (1N) and 1× with sodium chloride solution (sat.). The organic phase was dried and evaporated. The residue was purified by column chromatography on silica gel 40-63 μm, eluent ethyl acetate/n-hexane+1% TEA (3:1). 5'-O-(4,4',4''-tri(2-[2-Nitrophenyl]propyloxycarbonyloxy)triphenylmethyl)-$N^2$-isobutryldeoxyguanosine is obtained as a solid white foam. (Methylene chloride/methanol 5%+1% TEA): 0.22

Yield: 1.3 g≈7.0% of theory.
$^{13}$C-NMR: (125.75 MHz, CDCl$_3$, TMS): δ=17.63 (CH3-nppoc) 18.83 (CH3-ibu), 33.12 (CH-nppoc), 35.90 (CH-ibu), 39.89 (C-2'), 64.19 (C-5'), 70.97 (C-3'), 72.10 (CH2-nppoc), 83.90 (C-4'), 85.66 (C-trityl), 85.82 (C-1'), 120.31 (C-5), 120.34 (C-3,3',3'',5,5',5''-trityl), 124.21 (C-3-phenyl-nppoc), 127.61 (C-6-phenyl-nppoc), 128.25 (C-4-phenyl-nppoc), 129.57 (C-2,2',2'',6,6',6''-trityl), 132.78 (C-5-phenyl-nppoc), 136.47 (C-1-phenyl-nppoc), 137.74 (C-8), 140.82 (C-1,1',1''-trityl), 147.91 (C-4), 148.37 (C-2), 149.92 (C-2-phenyl-nppoc), 150.04 (O(CO)O), 153.19 (C-4,4',4''-trityl), 155.94 (C-6), 179.84 ppm (C=O-ibu).
$C_{63}H_{60}N_8O_{20}$: 1 249.22

1.20 5'-O-(4,4',4''-tri(2-[2-Nitrophenyl]propyloxycarbonyloxy)triphenylmethyl)-$N^6$-pivaloyldeoxyadenosine β-cyanoethyl-N,N-diisopropylaminophosphoamidite 1.0 g (0.80 mmol) of the 5'-triphenylmethyldeoxyadenosine derivative were dissolved in methylene chloride and 2.6 eq of ethyldiisopropylamine and cooled under protective gas to 0° C. Then 1.2 eq of chlorophosphine were added dropwise and stirred at 0° C. for 10 min. The mixture was stirred at RT for 1 h and the reaction was stopped with ethanol. It was then concentrated and dissolved in methylene chloride and extracted 2× with sodium bicarbonate solution (1N) and 1× with sodium chloride solution (sat.). The organic phase was dried and evaporated. The residue was purified by column chromatography with methylene chloride/methanol 2% on silica gel 40-63 μm. 5'-O-(4,4',4''-tri(2-[2-Nitrophenyl]propyloxycarbonyl-oxy)triphenylmethyl)-$N^6$-pivaloyldeoxyadenosine β-cyano-ethyl-N,N-diisopropylaminophosphoamidite is obtained as a solid white foam.

Yield: 0.7 g≈60% of theory.
$^{31}$P-NMR (202.45 MHz, CDCl$_3$): δ=149.37 ppm.

1.21 5'-O-(4,4',4''-tri(2-[2-Nitrophenyl]propyloxycarbonyloxy)triphenylmethyl)thymidine β-cyanoethyl-N,N-diisopropylaminophosphoamidite 2.0 g (1.73 mmol) of the 5'-triphenylmethylthymidine derivative were dissolved in methylene chloride and 2.6 eq of ethyldiisopropylamine and cooled under protective gas to 0° C. Then 1.2 eq of chlorophosphine were added dropwise and stirred at 0° C. for 10 min. The mixture was stirred at RT for 1 h and the reaction was stopped with ethanol. It was then concentrated and dissolved in methylene chloride and extracted 2× with sodium bicarbonate solution (1N) and 1× with sodium chloride solution (sat.). The organic phase was dried and evaporated. The residue was purified by column chromatography with ethyl acetate/hexane 1:1 on silica gel 40-63 μm. 5'-O-(4,4',4''-tri(2-[2-Nitrophenyl]-propyloxycarbonyloxy)triphenylmethyl)thymidine β-cyano-ethyl-N,N-diisopropylaminophosphoamidite is obtained as a solid white foam.

Yield: 2.1 g≈89% of theory.
$^{31}$P-NMR (202.45 MHz, CDCl$_3$): δ=149.77 ppm.

Example 2

Elimination of Protective Groups

The acid resistance of the nonactivated protective groups was carried out with 80% acetic acid and 1% trichloroacetic acid (standard conditions for oligonucleotide synthesis). Table 2 shows the result of this study.

All the samples are initially dissolved for 300 s or 900 s in 80% acetic acid and analyzed by HPLC. Those which withstand this treatment without ether cleavage are treated for 300 s or 900 s with 1% trichloroacetic acid and then analyzed.

TABLE 2

| Compound | Symbol | 80% acetic acid | 1% trichloroacetic acid |
|---|---|---|---|
| 5'-O-(4-Nppoc-trityl)-thymidine | S1 | stable | labile |
| 5'-O-(4-Methoxy-4'-Nppoc-trityl)thymidine | S2 | stable | labile |
| 5'-O-(4,4'-Dimethoxy-4''-Nppoc-trityl)-thymidine | S3 | labile | labile |
| 5'-O-(4,4'-diNppoc-trityl)thymidine | S4 | stable | labile |
| 5'-O-(4-Methoxy-4,4''-diNppoc-trityl)thymidine | S5 | stable | labile |
| 5'-O-(4,4',4''-triNppoc-trityl)thymidine | S6 | stable | Stable |

It is evident that the 4,4',4''-tri-Nppoc-trityl protective group (S6) is stable in trichloroacetic acid.

Example 3

Optimization of the Synthesis

A first optimization is achieved by using diphenylmethylchlorosilane in place of tert-butoxydiphenylchlorosilane.

Example 4

2 Solid-Phase Experiments

The two-stage protective groups are tested on a solid phase. The test of functionality in principle is carried out on a DNA processor D of febit ag in a Geniom® one apparatus.

5'-O-(4,4',4"-tri-Nppoc-trityl)thymidine phosphoamidite is condensed onto a silanized DNA processor surface. Spot illumination, subsequent acid treatment (max. 2 min) and coupling of a spacer are carried out. A detection is finally carried out once again.

The analogous experiment is carried out as control. However, in place of the amidite with the tandem protective group, an Nppoc-dT amidite is coupled. It was possible by this experiment to show the functionality of the two-stage protective group.

The invention claimed is:

1. A process for the synthesis of a nucleic acid by stepwise assembly of building blocks, wherein the building blocks are building blocks for the synthesis of a nucleic acid, wherein at least one of the building blocks carries a two-stage protective group, wherein the two-stage protective group contains a photoactivatable group selected from the group consisting of nitroveratryloxycarbonyl (NVOC), α-methyl-6-nitropiperonyloxycarbonyl (MeNPOC), 3,5-dimethoxybenzoincarbonate (DMBOC), 2-(o-nitrophenyl)propyloxycarbonyl (NPPOC), o-nitrobenzyl and 2-(o-nitrophenyl) ethyl, wherein the photoactivable group is removed by an illumination step and the remainder of the two-stage protective group is removed by a subsequent acid treatment step.

2. The process as claimed in claim 1, characterized in that the building block with the two-stage protective group has the general formula I:

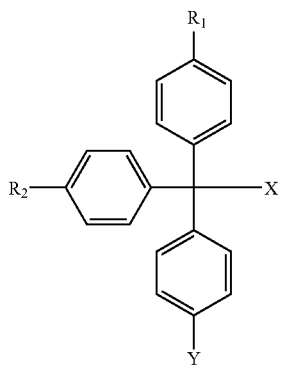

where $R_1$ and $R_2$ are each independently selected from hydrogen, $OR_3$, $O(CH_2)_n COOR_3$ and NHZ,
$R_3$ comprises a $C_1$-$C_8$ alkyl group, a $C_2$-$C_8$ alkenyl group, a $C_2$-$C_8$ alkynyl group or/and $C_6$-$C_{20}$ aryl group which may optionally have substituents,
X is the building block,
Y is in each case independently the photoactivatable group,
Z is an amino-protective group,
n is an integer from 0 to 4, and
where $R_1$ or/and $R_2$ may optionally be replaced by Y.

3. The process as claimed in claim 2, characterized in that a two-stage protective group which carries at least one fluorescent group is used.

4. The process as claimed in claim 3, characterized in that Y, $R_3$ or/and Z carry the fluorescent group.

5. The process as claimed in claim 1, characterized in that the building blocks are phosphoramidites.

6. The process as claimed in claim 5, characterized in that phosphoramidite building blocks carry the two-stage protective group on the 5'-O atom.

7. The process as claimed in claim 1, wherein at least one of the building blocks contains a spacer or linker group.

8. The process as claimed in claim 1, characterized in that the synthesis is carried out on a solid phase.

9. The process as claimed in claim 8, characterized in that a site-dependent synthesis of a plurality of nucleic acids, each with a different nucleotide sequence, is carried out on a single support.

10. A compound of the general formula I:

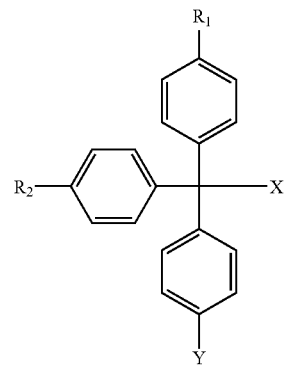

where $R_1$ and $R_2$ are each independently selected from hydrogen, $OR_3$, $O(CH_2)_n COOR_3$ and NHZ,
$R_3$ comprises a $C_1$-$C_8$ alkyl group, a $C_2$-$C_8$ alkenyl group, a $C_2$-$C_8$ alkynyl group or/and $C_6$-$C_{20}$ aryl group which may optionally have substituents,
X is a building block for the synthesis of a nucleic acid or a leaving group,
Y is in each case independently a photoactivatable group,
Z is an amino-protective group,
n is an integer from 0 to 4,
where $R_1$ or/and $R_2$ may optionally be replaced by Y, and
wherein the photoactivatable group is selected from the group consisting of nitroveratryloxycarbonyl (NVOC), α-methyl-6-nitropiperonyloxycarbonyl (MeNPOC), 3,5-dimethoxybenzoincarbonate (DMBOC), 2-(o-nitrophenyl)propyloxycarbonyl (NPPOC), o-nitrobenzyl and 2-(o-nitrophenyl) ethyl and wherein the photoactivatable group is removable by illumination.

11. The compound as claimed in claim 10, characterized in that it carries at least one fluorescent group.

12. The compound as claimed in claim 11, characterized in that Y, $R_3$ or/and Z carry a fluorescent group.

13. A method of synthesizing a nucleic acid from building blocks, wherein at least one of the building blocks is protected by a two-stage protective group, wherein the at least one of the building blocks protected by a two-stage protective group is a compound of Formula (I), said method comprising the steps of:
removing a photoactivatable group of the two-stage protective group by illumination, and
subsequently removing the rest of the two-stage protective group from the building block by acid treatment wherein formula (I) is

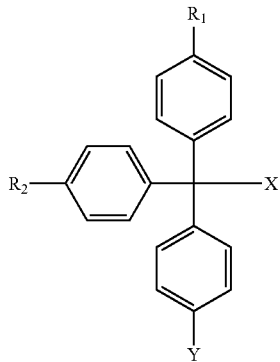

where $R_1$ and $R_2$ are each independently selected from hydrogen, $OR_3$, $O(CH_2)_n COOR_3$ and NHZ, $R_3$ comprises a $C_1$-$C_8$ alkyl group, a $C_2$-$C_8$ alkenyl group, a $C_2$-$C_8$ alkynyl group or/and $C_6$-$C_{20}$ aryl group which may optionally have substituents, X is a building block for the synthesis of a nucleic acid or a leaving group, Y is in each case independently a photoactivatable group, Z is an amino-protective group, n is an integer from 0 to 4, where $R_1$ or/and $R_2$ may optionally be replaced by Y, and wherein the photoactivatable group is selected from the group consisting of nitroveratryloxycarbonyl (NVOC), α-methyl-6-nitropiperonyloxycarbonyl (MeNPOC), 3,5-dimethoxybenzoincarbonate (DMBOC), 2-(o-nitrophenyl)propyloxycarbonyl (NPPOC), o-nitrobenzyl and 2-(o-nitrophenyl) ethyl and wherein the photoactivatable group is removable by illumination.

14. The process of claim 2, wherein the substituent is selected from the group consisting of a halogen, —OH, —SH, —O—, —S(O)—, —S(O)$_2$—, —NO$_2$, —CN and —NHZ, wherein Z is an amino-protective group.

15. The compound of claim 10, wherein the substituent is selected from the group consisting of a halogen, —OH, —SH, —O—, —S(O)—, —S(O)$_2$—, NO$_2$, —CN and —NHZ, wherein Z is an amino-protective group.

16. The method of claim 13, wherein the substituent is selected from the group consisting of a halogen, —OH, —SH, —O—, —S(O)—, —S(O)$_2$—, —NO$_2$, —CN and —NHZ, wherein Z is an amino-protective group.

17. The method of claim 13, characterized in that the compound of formula I carries at least one fluorescent group.

18. The method of claim 17, characterized in that Y, $R_3$ or/and Z carry a fluorescent group.

19. The compound of claim 10, characterized in that the building block is a phosphoramidite.

20. The compound of claim 19, characterized in that the linkage with the phosphoramidite building block is through the 5'-O atom.

21. The process of claim 13, characterized in that the building blocks are phosphoramidites.

22. The process of claim 21, characterized in that phosphoramidite building blocks carry the two-stage protective group on the 5'-O atom.

* * * * *